US008461090B2

(12) United States Patent
Glenn, Jr. et al.

(10) Patent No.: US 8,461,090 B2
(45) Date of Patent: *Jun. 11, 2013

(54) PERSONAL CARE COMPOSITION IN THE FORM OF AN ARTICLE HAVING A POROUS, DISSOLVABLE SOLID STRUCTURE

(75) Inventors: Robert Wayne Glenn, Jr., Liberty Township, OH (US); James Merle Heinrich, Fairfield, OH (US); Kathleen Mary Kaufman, Cincinnati, OH (US); John Robert Rusche, Cincinnati, OH (US); David Johnathan Kitko, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 53 days.

This patent is subject to a terminal disclaimer.

(21) Appl. No.: 12/633,257

(22) Filed: Dec. 8, 2009

(65) Prior Publication Data

US 2010/0179083 A1 Jul. 15, 2010

Related U.S. Application Data

(60) Provisional application No. 61/120,643, filed on Dec. 8, 2008.

(51) Int. Cl.
| | | |
|---|---|---|
| *C11D 17/00* | (2006.01) | |
| *C11D 1/12* | (2006.01) | |
| *C11D 1/14* | (2006.01) | |
| *C11D 1/29* | (2006.01) | |
| *A61K 8/02* | (2006.01) | |

(52) U.S. Cl.
USPC ........... 510/120; 510/127; 510/130; 510/141; 510/155; 510/156; 510/445; 510/475; 510/495; 510/498; 424/400

(58) Field of Classification Search
USPC ................. 510/120, 127, 130, 141, 155, 156, 510/445, 475, 495, 498; 424/400
See application file for complete search history.

(56) References Cited

U.S. PATENT DOCUMENTS

| | | | |
|---|---|---|---|
| 2,356,168 | A | 8/1944 | Mabley |
| 2,396,278 | A | 3/1946 | Lind |
| 2,438,091 | A | 3/1948 | Lynch |
| 2,486,921 | A | 11/1949 | Byerly |
| 2,486,922 | A | 11/1949 | Strain |
| 2,528,378 | A | 10/1950 | Mannheimer |
| 2,658,072 | A | 11/1953 | Kosmin |
| 2,694,668 | A | 11/1954 | Fricke |
| 2,809,971 | A | 10/1957 | Bernstein |
| 3,152,046 | A | 10/1964 | Kapral |
| 3,236,733 | A | 2/1966 | Karsten |
| 3,321,425 | A | 5/1967 | Blau |
| 3,332,880 | A | 7/1967 | Kessler |
| 3,426,440 | A | 2/1969 | Shen |
| 3,489,688 | A | 1/1970 | Pospischil |
| 3,653,383 | A | 4/1972 | Wise |
| 3,695,989 | A | 10/1972 | Albert |
| 3,753,196 | A | 8/1973 | Kurtz |
| 3,761,418 | A | 9/1973 | Parran, Jr. |
| 3,929,678 | A | 12/1975 | Laughlin |
| 3,967,921 | A | 7/1976 | Haberli |
| 4,020,156 | A | 4/1977 | Murray |
| 4,051,081 | A | 9/1977 | Jabs |
| 4,089,945 | A | 5/1978 | Brinkman |
| 4,196,190 | A | 4/1980 | Gehman |
| 4,197,865 | A | 4/1980 | Jacquet |
| 4,217,914 | A | 8/1980 | Jacquet |
| 4,272,511 | A | 6/1981 | Papantoniou |
| 4,323,683 | A | 4/1982 | Bolich, Jr. |
| 4,345,080 | A | 8/1982 | Bolich, Jr. |
| 4,379,753 | A | 4/1983 | Bolich, Jr. |
| 4,381,919 | A | 5/1983 | Jacquet |
| 4,422,853 | A | 12/1983 | Jacquet |
| 4,470,982 | A | 9/1984 | Winkler |
| 4,507,280 | A | 3/1985 | Pohl |
| 4,529,586 | A | 7/1985 | De Marco |
| 4,565,647 | A | 1/1986 | Llenado |
| 4,663,158 | A | 5/1987 | Wolfram |
| 4,710,374 | A | 12/1987 | Grollier |
| 4,822,613 | A | 4/1989 | Rodero |
| 4,885,107 | A | 12/1989 | Wetzel |
| 4,976,953 | A | 12/1990 | Orr et al. |
| 4,990,280 | A | 2/1991 | Thorengaard |
| 5,055,384 | A | 10/1991 | Kuhnert |
| 5,061,481 | A | 10/1991 | Suzuki |
| 5,062,889 | A | 11/1991 | Hohl |
| 5,094,853 | A | 3/1992 | Hagarty |
| 5,100,657 | A | 3/1992 | Ansher-Jackson |
| 5,100,658 | A | 3/1992 | Bolich, Jr. |
| 5,104,646 | A | 4/1992 | Bolich, Jr. |
| 5,106,609 | A | 4/1992 | Bolich, Jr. |
| 5,166,276 | A | 11/1992 | Hayama |
| 5,220,033 | A | 6/1993 | Kamei |
| 5,280,079 | A | 1/1994 | Allen |
| RE34,584 | E | 4/1994 | Grote |
| 5,391,368 | A | 2/1995 | Gerstein |
| 5,409,703 | A | 4/1995 | McAnalley |
| 5,429,628 | A | 7/1995 | Trinh et al. |
| 5,457,895 | A | 10/1995 | Thompson |
| 5,476,597 | A | 12/1995 | Sakata |
| 5,580,481 | A | 12/1996 | Sakata |

(Continued)

FOREIGN PATENT DOCUMENTS

| | | |
|---|---|---|
| CN | 1138091 A | 12/1996 |
| CN | 1219388 A | 6/1999 |

(Continued)

OTHER PUBLICATIONS

U.S. Appl. No. 61/472,941, filed Apr. 7, 2011, Glenn, Jr.

(Continued)

*Primary Examiner* — Lorna M Douyon
(74) *Attorney, Agent, or Firm* — Angela K. Haughey

(57) ABSTRACT

The present invention relates to a dissolvable article in the form of a porous dissolvable solid structure, comprising from about 23% to about 75% surfactant; wherein the surfactant has an average ethoxylate/alkyl ratio of from about 0.001 to about 0.45; from about 10% to about 50% water soluble polymer; and from about 1% to about 15% plasticizer; and wherein the article has a density of from about 0.05 g/cm³ to about 0.25 g/cm³.

25 Claims, No Drawings

U.S. PATENT DOCUMENTS

| | | | |
|---|---|---|---|
| 5,582,786 | A | 12/1996 | Brunskill |
| 5,660,845 | A | 8/1997 | Trinh |
| 5,672,576 | A | 9/1997 | Behrens |
| 5,674,478 | A | 10/1997 | Dodd |
| 5,750,122 | A | 5/1998 | Evans |
| 5,780,047 | A | 7/1998 | Kamiya |
| 5,955,419 | A | 9/1999 | Barket, Jr. |
| 6,010,719 | A | 1/2000 | Remon |
| 6,106,849 | A | 8/2000 | Malkan |
| 6,177,391 | B1 | 1/2001 | Zafar |
| 6,200,949 | B1 | 3/2001 | Reijmer |
| 6,458,754 | B1 | 10/2002 | Velazquez |
| 6,503,521 | B1 | 1/2003 | Atis |
| 6,790,814 | B1 | 9/2004 | Marin |
| 6,846,784 | B2 | 1/2005 | Engel |
| 6,943,200 | B1 | 9/2005 | Corrand |
| 7,015,181 | B2 * | 3/2006 | Lambino ............... 510/141 |
| 7,901,696 | B2 * | 3/2011 | Eknoian et al. ............ 424/400 |
| 2002/0064510 | A1 * | 5/2002 | Dalrymple et al. ........ 424/70.22 |
| 2002/0077264 | A1 | 6/2002 | Roberts |
| 2002/0081930 | A1 | 6/2002 | Jackson |
| 2002/0098994 | A1 | 7/2002 | Zafar |
| 2002/0099109 | A1 | 7/2002 | Dufton |
| 2002/0177621 | A1 | 11/2002 | Hanada |
| 2002/0187181 | A1 | 12/2002 | Godbey |
| 2003/0032573 | A1 | 2/2003 | Tanner |
| 2003/0045441 | A1 | 3/2003 | Hsu |
| 2003/0069154 | A1 | 4/2003 | Hsu |
| 2003/0080150 | A1 | 5/2003 | Cowan |
| 2003/0099691 | A1 | 5/2003 | Lydzinski |
| 2003/0099692 | A1 | 5/2003 | Lydzinski |
| 2003/0180242 | A1 * | 9/2003 | Eccard et al. ............. 424/70.11 |
| 2003/0186826 | A1 | 10/2003 | Eccard |
| 2003/0194416 | A1 | 10/2003 | Shefer |
| 2003/0199412 | A1 | 10/2003 | Gupta |
| 2003/0207776 | A1 | 11/2003 | Shefer |
| 2003/0215522 | A1 | 11/2003 | Johnson |
| 2003/0232183 | A1 | 12/2003 | Dufton |
| 2004/0029762 | A1 | 2/2004 | Hensley |
| 2004/0032859 | A1 | 2/2004 | Miao |
| 2004/0048759 | A1 | 3/2004 | Ribble |
| 2004/0053808 | A1 | 3/2004 | Raehse |
| 2004/0071742 | A1 | 4/2004 | Popplewell |
| 2004/0071755 | A1 | 4/2004 | Fox |
| 2004/0108615 | A1 | 6/2004 | Foley |
| 2004/0110656 | A1 | 6/2004 | Casey |
| 2004/0126585 | A1 | 7/2004 | Kerins |
| 2004/0175404 | A1 | 9/2004 | Shefer |
| 2004/0202632 | A1 | 10/2004 | Gott |
| 2004/0206270 | A1 | 10/2004 | Vanmaele |
| 2004/0242772 | A1 | 12/2004 | Huth |
| 2005/0069575 | A1 | 3/2005 | Fox |
| 2005/0118237 | A1 | 6/2005 | Krzysik |
| 2005/0136780 | A1 | 6/2005 | Clark |
| 2005/0137272 | A1 | 6/2005 | Gaserod |
| 2005/0202992 | A1 | 9/2005 | Grandio Portabales |
| 2005/0220745 | A1 | 10/2005 | Lu |
| 2005/0232954 | A1 | 10/2005 | Yoshinari |
| 2005/0272836 | A1 | 12/2005 | Yaginuma |
| 2005/0287106 | A1 | 12/2005 | Legendre |
| 2006/0002880 | A1 * | 1/2006 | Peffly et al. ................. 424/70.13 |
| 2006/0052263 | A1 | 3/2006 | Roreger |
| 2006/0228319 | A1 | 10/2006 | Vona |
| 2007/0028939 | A1 | 2/2007 | Mareri |
| 2007/0149435 | A1 | 6/2007 | Koenig |
| 2007/0225388 | A1 | 9/2007 | Cooper |
| 2008/0035174 | A1 | 2/2008 | Aubrun-Sonneville |
| 2008/0090939 | A1 | 4/2008 | Netravali |
| 2008/0131695 | A1 | 6/2008 | Aouad |
| 2008/0138492 | A1 | 6/2008 | Cingotti |
| 2008/0152894 | A1 | 6/2008 | Beihoffer |
| 2008/0215023 | A1 | 9/2008 | Scavone |
| 2008/0293839 | A1 | 11/2008 | Stobby |
| 2009/0232873 | A1 * | 9/2009 | Glenn et al. ............... 424/443 |
| 2009/0263342 | A1 * | 10/2009 | Glenn et al. ............... 424/70.11 |
| 2010/0167971 | A1 | 7/2010 | Glenn, Jr. |
| 2010/0173817 | A1 | 7/2010 | Glenn, Jr. |
| 2010/0279905 | A1 | 11/2010 | Glenn, Jr. |
| 2010/0286011 | A1 | 11/2010 | Glenn, Jr. |
| 2010/0291165 | A1 | 11/2010 | Glenn, Jr. |
| 2010/0298188 | A1 | 11/2010 | Glenn, Jr. |
| 2011/0023240 | A1 | 2/2011 | Fossum |
| 2011/0028373 | A1 | 2/2011 | Fossum |
| 2011/0028374 | A1 | 2/2011 | Fossum |
| 2011/0182956 | A1 | 7/2011 | Glenn, Jr. |
| 2011/0189246 | A1 | 8/2011 | Glenn, Jr. |
| 2011/0189247 | A1 | 8/2011 | Glenn, Jr. |
| 2011/0195098 | A1 | 8/2011 | Glenn, Jr. |
| 2012/0021026 | A1 | 1/2012 | Glenn, Jr. |

FOREIGN PATENT DOCUMENTS

| | | | |
|---|---|---|---|
| CN | 1268558 | A | 10/2000 |
| CN | 1357613 | A | 7/2002 |
| CN | 1530431 | A | 9/2004 |
| CN | 1583991 | A | 2/2005 |
| DE | 19607851 | A1 | 9/1997 |
| DE | 10331767 | A1 | 2/2005 |
| EP | 609808 | A1 | 8/1994 |
| EP | 0858828 | A1 | 8/1998 |
| EP | 1160311 | B1 | 12/2001 |
| EP | 1217987 | B1 | 12/2004 |
| EP | 2085434 | A1 | 8/2009 |
| FR | 2871685 | A | 12/2005 |
| FR | 2886845 | A | 12/2006 |
| GB | 2235204 | A | 2/1991 |
| GB | 2355008 | A | 4/2001 |
| JP | 58021608 | A | 2/1983 |
| JP | 58216109 | A | 12/1983 |
| JP | 62072609 | A | 4/1987 |
| JP | 62072610 | A | 4/1987 |
| JP | 1313418 | A | 12/1989 |
| JP | 5344873 | A | 12/1993 |
| JP | 6017083 | A | 1/1994 |
| JP | 7089852 | A | 4/1995 |
| JP | 8325133 | A | 12/1996 |
| JP | 10251371 | A | 9/1998 |
| JP | 2003073700 | A | 3/2003 |
| JP | 2003082397 | A | 3/2003 |
| JP | 2004345983 | A | 12/2004 |
| JP | 2005171063 | A | 6/2005 |
| JP | 2007197540 | A | 8/2007 |
| JP | 2007091954 | A | 12/2007 |
| KR | 20020003442 | | 1/2002 |
| WO | WO9514495 | A1 | 6/1995 |
| WO | WO01/24770 | A1 | 4/2001 |
| WO | WO 2004/032859 | A | 4/2004 |
| WO | WO2004/041991 | A1 | 5/2004 |
| WO | WO2005/003423 | A1 | 1/2005 |
| WO | WO2007033598 | A1 | 3/2007 |
| WO | WO2007/093558 | A2 | 8/2007 |
| WO | WO2009019571 | | 2/2009 |

OTHER PUBLICATIONS

P&G Case 11200M ISR dated May 6, 2011, PCT/US2009/067130, 5 pages.
P&G Case 11201M ISR dated May 4, 2011, PCT/US2009/067088, 5 pages.
P&G Case 11201M ISR dated Jul. 19, 2011, PCT/US2009/067088, 7 pages.
P&G Case 11202M3 ISR dated May 9, 2011, PCT/US2009/067132, 5 pages.
P&G Case 11202M2 ISR dated Jul. 20, 2011, PCT/US2009/067131, 5 pages.
P&G Case 11202M ISR dated Apr. 29, 2011, PCT/US2009/067089, 5 pages.
P&G Case 10997M ISR dated Jul. 15, 2009, PCT/IB2009/050388, 8 pages.
P&G Case 11037M ISR dated Aug. 17, 2009, PCT/US2009/040739, 6 pages.
P&G Case 11037M ISR dated Nov. 4, 2009, PCT/US2009/040739, 10 pages.
P&G Case 11199M ISR dated Dec. 15, 2011, PCT/US2009/067087, 5 pages.
P&G Case 11203M ISR dated Jul. 19, 2011, PCT/US2009/067133, 4 pages.

P&G Case 11200M ISR dated Jul. 19, 2011, PCT/US2009/067130, 7 pages.
P&G Case 11494M ISR dated Apr. 27, 2011, PCT/US2010/059365, 5 pages.
P&G Case 11495M ISR dated Apr. 27, 2011, PCT/US2010/059455, 5 pages.
P&G Case 11523M ISR dated Apr. 27, 2011, PCT/US2010/059359, 5 pages.
T. Hildebrand, P. Rüegsegger. "Quantification of bone microarchitecture with the structure model index." Computer Methods in Biomechanics and Biomedical Engineering 1997; 1:15-23.
Vesterby, A.; Star volume in bone research. A histomorphometric analysis of trabecular bone structure using vertical sections; Anat Rec.; Feb. 1993; 235(2): 325-334.
C. D. Vaughan. Solubility, Effects in Product, Package, Penetration and Preservation, Cosmetics and Toiletries, vol. 103, Oct. 1988.
*Encyclopedia of Polymer Science and Engineering*, vol. 15, 2d ed., pp. 204-308, John Wiley & Sons, Inc. (1989).
Anonymous: "P8136 Poly(vinyl alcohol)" Internet article, [Online] XP002538935 Retrieved from the Internet: URL:http://www.sigmaaldrich.com/catalog/ProductDetail.do?D7=0&N25=SEARCH_CONCAT_PNO%7CBRAND_KEY&N4=P8136%7CSIAL&N25=0&QS=0N&F=SPEC> [retrieved on Jul. 28, 2009].
M. K. Industires (Gujarat India, http://www.soapstrips.com).
Sanipro Sanitary Products (Italy, http://www.sanipro.it).
Adhesives Research (Pennsylvania, http://12.4.33.51/news/apresmed.htm).
Solublon (Toyohashi Japan, http://www.solublon.com).
SPI Pharma (Delaware, http://www.spipharma.com).
Wenda (China, http://www.wenda.com).
MOVA Pharmaceutical and Kosmos (USA, http://www.icon-pr.com/news/news_print.cfm?inv_id=266-1).
Cima Labs, Inc. (Minnesota, http://www.cimalabs.com/).
Cardinal Health (Dublin, Ohio, http://spd.cardinal.com/).
Le Laboratoire du Bain (France, http://www.labodubain.com/).
Amerilab Technologies, Inc. (Minnesota, http://www.amerilabtech.com/).
Meguiar's Car Wash Strips: (Meguiar's Inc. California, http://www.automotivedigest.com/view_art.asp?articlesID=12414).
Pure Soap Leafz: (Soap UNTLD, Netherlands, http://www.upandunder.co.uk/eshop/catalogue/testbs.asp?Manufacturer_ID=252&Activity_ID=33&Description_ID=157).
Dissolving Soap Strips (Ranir LLC, Michigan, www.ranir.com).
Japanese Paper Soap (http://www.wishingfish.com/papersoap.html).
Travelers Passport Paper Soap Sheets (http://www.weddingfavorsnow.com/index.asp?PageAction=VIEWPROD&ProdID=510).
Office Action for U.S. Appl. No. 12/424,812 dated Nov. 1, 2011; P&G Case 11037M; Glenn, Jr. et al.; filing date Apr. 16, 2009.
Office Action for U.S. Appl. No. 12/633,228 dated May 11, 2011; P&G Case 11199M; Glenn, Jr. et al.; filing date Dec. 8, 2009.
Office Action for U.S. Appl. No. 12/633,228 dated Oct. 25, 2011; P&G Case 11199M; Glenn, Jr. et al.; filing date Dec. 8, 2009.
Office Action for U.S. Appl. No. 12/633,257 dated Jun. 1, 2011; P&G Case 11200M; Glenn, Jr. et al.; filing date Dec. 8, 2009.
Office Action for U.S. Appl. No. 12/633,257 dated Nov. 17, 2011; P&G Case 11200M; Glenn, Jr. et al.; filing date Dec. 8, 2009.
Office Action for U.S. Appl. No. 12/633,301 dated Jun. 3, 2011; P&G Case 11201M; Glenn, Jr. et al.; filing date Dec. 8, 2009.
Office Action for U.S. Appl. No. 12/633,301 dated Nov. 7, 2011; P&G Case 11201M; Glenn, Jr. et al.; filing date Dec. 8, 2009.
Office Action for U.S. Appl. No. 12/633,550 dated Nov. 16, 2011; P&G Case 11202M; Glenn, Jr. et al.; filing date Dec. 8, 2009.
Office Action for U.S. Appl. No. 12/633,335 dated Jul. 8, 2011; P&G Case 11202M2; Glenn, Jr. et al.; filing date Dec. 8, 2009.
Office Action for U.S. Appl. No. 12/633,415 dated Nov. 14, 2011; P&G Case 11202M3; Glenn, Jr. et al.; filing date Dec. 8, 2009.
Office Action for U.S. Appl. No. 12/633,572 dated Jul. 28, 2011; P&G Case 11203M; Glenn, Jr. et al.; filing date Dec. 8, 2009.
Office Action for U.S. Appl. No. 12/361,634 dated Sep. 14, 2011; P&G Case 10997M; Glenn, Jr. et al.; filing date Jan. 29, 2009.

* cited by examiner

PERSONAL CARE COMPOSITION IN THE FORM OF AN ARTICLE HAVING A POROUS, DISSOLVABLE SOLID STRUCTURE

CROSS REFERENCE TO RELATE APPLICATION

This application claims the benefit of U.S. Provisional Application Ser. No. 61/120,643 filed Dec. 8, 2008, which is incorporated by reference herein.

FIELD OF THE INVENTION

The present invention relates to personal care compositions, especially those personal care compositions in the form of an article that is a porous, dissolvable solid structure, delivering consumer desired lathering.

BACKGROUND OF THE INVENTION

The majority of personal care products in the market today are sold as liquid products. While widely used, liquid products have disadvantages in terms of packaging, storage, transportation, and convenience of use.

Liquid personal care products typically are sold in bottles which add significant cost as well as packaging waste, much of which ends up in land-fills. Liquid personal care products also usually comprise a substantial amount of water in the formula which adds significant weight and size translating into greater shipping and storage costs. Liquid personal care products can also be difficult to use in terms of controlling dosage and the delivery of the product.

Consumers using personal care products desire amounts of lather and dose or weight of the product adequate to wash the hair and/or body. It has been found that a technical challenge exists in delivering a lather performance in a porous dissolvable solid product equal to a liquid personal care product.

It is an object of the present invention to provide a dissolvable solid personal care product that can deliver a consumer desirable lather performance (with equal performance to today's liquid products). It is a further object of the present invention to provide such a product that can be produced in an economical manner via physical aeration followed by drying.

Additionally, it is an object of the present invention to provide a dissolvable solid personal care product that can be conveniently and quickly dissolved in the palm of the consumer to constitute a liquid product for ease of application to hair/skin while providing sufficient topical delivery of active agents for whole head hair and whole body skin applications (with similar performance as today's liquid products).

SUMMARY OF THE INVENTION

A dissolvable article in the form of a porous dissolvable solid structure, comprising from about 23% to about 75% surfactant; wherein the surfactant has an average ethoxylate/alkyl ratio of from about 0.001 to about 0.45; from about 10% to about 50% water soluble polymer; and from about 1% to about 15% plasticizer; and wherein the article has a density of from about 0.05 g/cm3 to about 0.25 g/cm3.

A pre-mix suitable for use in making a dissolvable article that is in the form of a porous dissolvable solid structure, wherein the pre-mix comprises from about 3% to about 20% water soluble polymer; from about 0.3% to about 7% plasticizer; from about 8% to about 30% surfactant; wherein the surfactant has an average ethoxylate/alkyl ratio of from about 0.001 to about 0.45; and wherein the pre-mix has from about 20% to about 50% solids, and a viscosity of from about 5000 cps to about 150,000 cps.

A dissolvable article in the form of a porous dissolvable solid structure, wherein the article is formed by a process comprising the steps of preparing a pre-mix, wherein the pre-mix comprises a surfactant, a water soluble polymer, a plasticizer, one or more surfactants wherein the surfactant has an average ethoxylate/alkyl ratio of from about 0.001 to about 0.45, and wherein the pre-mix has from about 20% to about 50% solids and a viscosity of from about 5,000 cps to about 150,000 cps; aerating the pre-mix by introducing a gas into the pre-mix to form a wet aerated pre-mix; forming the wet aerated pre-mix into a desired one or more shapes to form a shaped wet pre-mix; and forming the dissolvable article by drying the shaped wet pre-mix into a final moisture content, wherein the final moisture content is from about 0.1% to about 25% moisture.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Definitions

The flexible porous dissolvable solid structure article may be referred to herein as "the Article" or "the Dissolvable Article". All references are intended to mean the flexible dissolvable porous solid structure article.

As used herein, "dissolvable" means that the flexible porous dissolvable solid structure article meets the hand dissolution value in order to be considered dissolvable within the context of this application.

Hand Dissolution Method: One pad with dimensions as specified in the examples (approximately 0.8 grams to 1.20 grams) of the dissolvable porous solid is placed in the palm of the hand while wearing nitrile gloves. 7.5 cm³ of luke warm tap water (from about 30° C. to about 35° C.) is quickly applied to the product via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum.

As used herein "porous solid structure" means a solid, interconnected, polymer-containing matrix that defines a network of spaces or cells that contain a gas, typically a gas such as air without collapse of the foam structure during the drying process, thereby maintaining the physical strength and cohesiveness of the solid.

To measure the Cell Wall Thickness and the cell interconnectivity via the Star Volume and the Structure Model Index, disk-like samples, approximately 4 cm in diameter and 3 to 7 mm high, are scanned using a micro computed tomography system (μCT80, SN 06071200, Scanco Medical AG). Each sample is imaged while sitting flat on the bottom of a cylindrical tube. Image acquisition parameters are 45 kVp, 177 μA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 μm. For data analysis, a volume of interest is selected to be fully within the sample, avoiding the surface region. A typical volume of interest is 1028×772×98 voxels.

Cell Wall Thickness is measured according to the method defined for the measurement of Trabecular Thickness using Scanco Medical's Bone Trabecular Morphometry evaluation. The definition of Trabecular Thickness as taken from the Scanco User's manual: Trabecular Thickness uses a Euclidean distance transformation (EDM), which calculates the Euclidean distance from any point in the foreground to the nearest background point. The Trabecular Thickness measure represents twice the centerline values associated with the local maxima of the EDM, which represents the distance to the center of the object (twice this distance will yield the thickness).

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 - \frac{BV - \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, StarVolume measurements are made. Star Volume is a measure of the "openness" of the void space in a two phase structure. By choosing a random uniformly distributed set of points in the phase of interest (in our case this is the background), we can extend lines in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (we only want to accept lines that actually intersect with the foreground phase). The final equation is based upon the research published in *Star volume in bone research. A histomorphometric analysis of trabecular bone structure using vertical sections*; Vesterby, A.; Anat Rec.; 1993 February; 235(2):325-334.:

$$StarVolume = \frac{4}{3}\pi \cdot \frac{\sum dist^3}{N}$$

where dist is the individual distances and N is the number of lines examined.

The Percent Open Cell Content is measured via gas pycnometry. Gas pycnometry is a common analytical technique that uses a gas displacement method to measure volume accurately. Inert gases, such as helium or nitrogen, are used as the displacement medium. The sample is sealed in the instrument compartment of known volume, the appropriate inert gas is admitted, and then expanded into another precision internal volume. The pressure before and after expansion is measured and used to compute the sample volume. Dividing this volume into the sample weight gives the gas displacement density.

ASTM Standard Test Method D2856 provides a procedure for determining the percentage of open cells using an older model of an air comparison pycnometer. This device is no longer manufactured. However, you can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials.

For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the true volume as measured by the Accupyc. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

The Specific Surface Area is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the degassed sample+sample tube weight. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved.

Sample Preparation (Degassing): A sample not adequately cleaned of adsorbed contaminants will outgas during an analysis and some portion of the surface will be inaccessible to measurement. The purpose of degassing is to remove these adsorbed molecules from the surface of the sample prior to analysis. Adsorptive molecules must reach all parts of the surface for the true surface area to be revealed. Samples are prepared by heating the sample while simultaneously evacuating the sample tube.

For these experiments, the samples are outgassed under evacuation at room temperature overnight. Samples may then analyzed using an ASAP 2420 with krypton gas adsorption. Krypton gas is preferred over nitrogen gas as it has a saturation pressure approximately 1/300 that of nitrogen at liquid nitrogen temperature (krypton: 2.5 torr; nitrogen: 760 torr). Therefore, compared to nitrogen, there is in the free space above the sample about 1/300 the number of krypton molecules present at the same relative pressure. Since about the same number of krypton and nitrogen molecules are required to form a monolayer, this number represents a far greater proportion of the quantity dosed than in the case of nitrogen. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

The density of the Article is determined by the equation: Calculated Density=Basis Weight of Article/(Article Thickness×1,000). The Basis Weight and Thickness of the Article are determined in accordance with the methodologies described herein.

The thickness of the dissolvable porous solid (i.e., substrate or sample substrate) is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 psi (6.32 µm/cm²).

The thickness of the dissolvable porous solid is measured by raising the platen, placing a section of the sample substrate on the stand beneath the platen, carefully lowering the platen to contact the sample substrate, releasing the platen, and measuring the thickness of the sample substrate in millimeters on the digital readout. The sample substrate should be fully extended to all edges of the platen to make sure thickness is measured at the lowest possible surface pressure, except for the case of more rigid substrates which are not flat. For more rigid substrates which are not completely flat, a flat edge of the substrate is measured using only one portion of the platen impinging on the flat portion of the substrate.

The Basis Weight, as used herein, means a basis weight calculated as the weight of the dissolvable porous solid component per area of the selected dissolvable porous solid (grams/m²). The area is calculated as the projected area onto a flat surface perpendicular to the outer edges of the porous solid. For a flat object, the area is thus computed based on the area enclosed within the outer perimeter of the sample. For a spherical object, the area is thus computed based on the average diameter as $3.14 \times (\text{diameter}/2)^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (preferably shaded-in for contrast) including a scale and using image analysis techniques.

The density of the dissolvable porous solid is determined by the equation: Calculated Density=Basis Weight of porous solid/(Porous Solid Thickness×1,000). The Basis Weight and Thickness of the dissolvable porous solid are determined in accordance with the methodologies described herein.

The Scanning Electron Microscope (SEM) Imaging is performed by the following method: Representative sections are cut from the sponge with a clean razor blade and mounted with the cut face up on a standard cryo-SEM stub. Samples are secured onto the stub with carbon tape and silver paint. Samples are imaged using an Hitachi S-4700 FE-SEM fitted with a Gatan Alto 2500 cryo stage. Samples are cooled to −95dC before imaging in the microscope. Samples are lightly coated with Platinum to reduce charging. Representative images are collected at 2 kV, 20uA extraction voltage, ultra high resolution mode using the lower secondary electron detector. Long working distances are used to allow the entire sample to be imaged in one frame.

The Dissolvable Article

The present inventors have found that Dissolvable Article can be prepared such that the Dissolvable Article can be conveniently and quickly dissolved in the palm of the consumer resulting in a liquid product. Once dissolved, this product can be used in a manner similar to a conventional liquid product, i.e. applied to the skin and/or hair. It has been found that such Dissolvable Article can now deliver lather equal to that of today's liquid products.

The Dissolvable Article has a hand dissolution value of from about 1 to about 30 strokes, in one embodiment from about 2 to about 25 strokes, in another embodiment from about 3 to about 20 strokes, and in still another embodiment from about 4 to about 15 strokes.

The Dissolvable Article has a maximum Cell Wall Thickness. The Article has a Cell Wall Thickness of from about from about 0.02 mm to about 0.12 mm, in one embodiment from about 0.025 mm to about 0.10 mm, in another embodiment from about 0.03 mm to about 0.08 mm, and in still another embodiment from about 0.035 mm to about 0.06 mm.

The Dissolvable Article has a minimum level of interconnectivity between the cells, which is quantified by both the Star Volume, the Structure Model Index (SMI), and the Percent Open Cell Content. The Article has a Star Volume of from about 1 mm³ to about 90 mm³, in one embodiment from about 2 mm³ to about 70 mm³, in another embodiment from about 3 mm³ to about 50 mm³, and in still another embodiment from about 4 mm³ to about 30 mm³ The Dissolvable Article has a non-negative Structure Model Index of from about 0.0 to about 3.0, in one embodiment from about 1.0 to about 2.95, and in another embodiment from about 1.5 to about 2.90. The Dissolvable Article has a Percent Open Cell Content of from about 80% to 100%, in one embodiment from about 85% to about 97.5%, and in another embodiment from about 90% to about 95%.

The Dissolvable Article also has a minimum Specific Surface Area. The Dissolvable Article has a Specific Surface Area of from about 0.03 m²/g to about 0.20 m²/g, in one embodiment from about 0.035 m²/g to about 0.18 m²/g, in another embodiment from about 0.04 m²/g to about 0.16 m²/g, and in still another embodiment from about 0.045 m²/g to about 0.14 m²/g.

In one embodiment the Dissolvable Article is a flat, flexible substrate in the form of a pad, a strip or tape and having a thickness of from about 0.5 mm to about 10 mm, in one embodiment from about 1 mm to about 9 mm, in another embodiment from about 2 mm to about 8 mm, and in a further embodiment from about 3 mm to about 7 mm as measured by the below methodology. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

The Dissolvable Article has a basis weight of from about 125 grams/m² to about 3,000 grams/m², in one embodiment from about 200 grams/m² to about 2,500 grams/m², in another embodiment from about 300 grams/m² to about 2,000 grams/m², and in still another embodiment from about 400 grams/m² to about 1,500 grams/m².

The Dissolvable Article has a wet density of from about 0.15 g/cm³ to about 0.50 g/cm³, in one embodiment from about 0.20 g/cm³ to about 0.45 g/cm³, in another embodiment from about 0.25 g/cm³ to about 0.40 g/cm³, and in yet another embodiment from about 0.30 g/cm³ to about 0.35 g/cm³.

The Dissolvable Article has a dry density of from about 0.05 g/cm³ to about 0.40 g/cm³, in another embodiment from about 0.08 g/cm³ to about 0.30 g/cm³, and in yet another embodiment from about 0.10 g/cm³ to about 0.25 g/cm³, and in yet another embodiment from about 0.12 g/cm³ to about 0.20 g/cm³.

Consumers desire personal care products to deliver a certain amount of lather performance. When the same surfactant system used in liquid personal care products is included in a Dissolvable Article, the Dissolvable Article delivers less lather performance (See Table 1). As shown in Table 1 both the liquid shampoo and the Dissolvable Article comprise the same surfactants and the same proportions. Additionally, the Dissolvable Article is applied to the hair at a lower dosage so that both the products (the Dissolvable Article and the liquid shampoo) deliver the same surfactant dosage to the hair (0.14 grams of surfactant). However, as shown by the hair lather volume the Dissolvable Article delivers approximately 67% of the lather volume vs the liquid shampoo. In Table 1 the surfactants are represented as follows Ammonium Laureth-3 Sulfate as C12E3S; Ammonium Lauryl Sulfate as C12S; Cocamide Monoethanolamine as CMEA; and Cetyl Alcohol as Cetyl Alcohol. The lather data is collected by the method as described herein.

TABLE 1

|  | Retail liquid hair shampoo product (Example 2) | Dissolving porous shampoo solid (Example 10.1) |
|---|---|---|
| Surfactant Ratio of C12E3S/C12S/CMEA/Cetyl Alcohol | 1.0/0.6/0.15/0.09 | 1.0/0.6/0.15/0.09 |
| Ethoxylate/Alkyl Ratio | 0.46 | 0.46 |
| C9-C11/C12-C16 Ratio | 0.02 | 0.02 |
| Surfactant Concentration | 18.4 wt. % | 61.3 wt. % |
| Product Density | 1.0 g/cm³ | 0.06 g/cm³ |
| Dissolution Performance | Not Required | 6 strokes |
| Hair Application Product Dosage | 0.75 g | 0.22 g |
| Hair Application Surfactant Dosage | 0.14 g | 0.14 g |
| Hair Lather Volume | 91 ml | 61 ml |
| Hair Lather Volume Index | 100% | 67% |

It has been found that the surfactant system of the present invention can deliver the consumer desired lather performance from a Dissolvable Article, similar to that of today's liquid personal care products.

It has been surprisingly found that the level of ethoxylation in the surfactant system, in particular a lower ethoxylate to alkyl ratio, delivers higher levels of lather in a Dissolvable Article. It has also been observed that a minimum level of ethoxylation delivers consumer desired flexibility and softness of the Dissolvable Articles of the present invention. While not being limited by theory, it is believed that this could be due to interaction synergies between the ethoxlate groups on the surfactants and the water soluble polymer, giving rise to greater plasticization of the polymer.

It has been additionally found that the lather performance of a Dissolvable Article can be further improved by choosing a particular carbon chain length, in particular increasing the C9-C11/C12-C16 chain length ratio.

The surfactant system of the present invention results in greater lather volume than Dissolvable Articles comprising a conventional surfactant system. For example a Dissolvable Article having a standard surfactant ethoxylate to alkyl ratio of about 0.46 can generate about 67% lather volume index (see example 10.1 in Table 2) whereas a Dissolvable Article comprising the inventive surfactant system with a ethoxylate to alkyl ratio of about 0.11 can generate about 87% lather volume index (see example 14.1 of Table 2). Additionally, further examples are at Table 3 for higher density Articles. See example 10.2 having an ethoxylate to alkyl ratio of about 0.46 vs. example 14.2 having an ethoxylate to alkyl ratio of about 0.11. One can also see lather improvement resulting from a higher C9-C11/C12-16 chain length ratio. For example, a Dissolvable Article having a standard surfactant ethoxylate to alkyl ratio of 0.46 and a C9-C11/C12-C16 ratio of 0.02 can generate about 67% lather volume index (see example 10.1 in Table 2) whereas a Dissolvable Article comprising a surfactant ethoxylate to alkyl ratio of 0.48 and a C9-C11/C12-C16 ratio of 0.17 can generate about 79% lather volume index (see example 12.1 of Table 2). Additionally, further examples are at Table 3 for higher density Articles. See example 10.2 having a surfactant ethoxylate to alkyl ratio of 0.48 and a C9-C11/C12-C16 ratio of 0.17 vs. example 12.2 having a surfactant ethoxylate to alkyl ratio of 0.48 and a C9-C11/C12-C16 ratio of 0.17. One can also see a Dissolvable Article comprising the inventive surfactant system with a low ethoxylate to alkyl ratio of about 0.18 and a high C9-C11/C12-C16 ratio of 0.83 which can generate about 95% lather volume index (see example 15.1 of Table 2). Additionally, a further example is at Table 3 showing Dissolvable Articles having a higher density. In one example (see example 15.2 in Table 3) the surfactant ethoxylate to alkyl ratio is 0.18 and the C9-C11/C12-C16 ratio is 0.83. This example (15.2) generates about 103% lather volume index.

TABLE 2

Dissolution/Lather Performance from Lower Density Pads (prepared from 0.17 to 0.19 wet density foams)

| Example | Average Ratio of Ethoxylate/Alkyl | Average Ratio of C9-C11/C12-C16 Alkyl | Product Surfactant Weight % | Hair Surfactant Dosage | Lather Volume Index | Hand Dissolution |
|---|---|---|---|---|---|---|
| Ex. 2 | 0.46 | 0.02 | 18% | 0.14 g | 100% (91 ml) | — |
| Ex. 10.1 | 0.46 | 0.02 | 61.3%[1] | 0.14 g | 67% | 6 strokes |
| Ex. 11.1 | 0.26 | 0.02 | 61.3%[1] | 0.14 g | 77% | 4 strokes |
| Ex. 12.1 | 0.48 | 0.17 | 61.0%[1] | 0.14 g | 79% | 6 strokes |

TABLE 2-continued

Dissolution/Lather Performance from Lower Density Pads (prepared from 0.17 to 0.19 wet density foams)

| Example | Average Ratio of Ethoxylate/Alkyl | Average Ratio of C9-C11/C12-C16 Alkyl | Product Surfactant Weight % | Hair Surfactant Dosage | Lather Volume Index | Hand Dissolution |
|---|---|---|---|---|---|---|
| Ex. 13.1 | 0.27 | 0.17 | 61.0%[1] | 0.14 g | 79% | 4 strokes |
| Ex. 14.1 | 0.11 | 0.16 | 61.0%[1] | 0.14 g | 87% | 6 strokes |
| Ex. 15.1 | 0.18 | 0.83 | 61.4%[1] | 0.14 g | 95% | 6 strokes |

[1]Calculated weight % of surfactant in dry solid assuming 5% residual moisture content.

TABLE 3

Dissolution/Lather Performance from Lower Density Pads (prepared from 0.20 to 0.23 wet density foams)

| Example | Average Ratio of Ethoxylate/Alkyl | Average Ratio of C9-C11/C12-C16 Alkyl | Product Surfactant Weight % | Hair Surfactant Dosage | Lather Volume Index | Hand Dissolution |
|---|---|---|---|---|---|---|
| Ex. 2 | 0.46 | 0.02 | 18% | 0.14 g | 100% (91 ml) | — |
| Ex. 10.2 | 0.46 | 0.02 | 61.3%[1] | 0.14 g | 68% | 6 strokes |
| Ex. 11.2 | 0.26 | 0.02 | 61.3%[1] | 0.14 g | 78% | 4 strokes |
| Ex. 12.2 | 0.48 | 0.17 | 61.0%[1] | 0.14 g | 77% | 6 strokes |
| Ex. 13.2 | 0.27 | 0.17 | 61.0%[1] | 0.14 g | 82% | 6 strokes |
| Ex. 14.2 | 0.11 | 0.16 | 61.0%[1] | 0.14 g | 104% | 6 strokes |
| Ex. 15.2 | 0.18 | 0.83 | 61.4%[1] | 0.14 g | 103% | 8 strokes |

[1]Calculated weight % of surfactant in dry solid assuming 5% residual moisture content Surfactant System The Dissolvable Article of the present invention comprises from about 23% to about 75% of surfactant by weight of the total composition. In another embodiment, the Dissolvable Article comprises from about 50% to about 70% surfactant by weight of the total composition. In one embodiment the surfactant system of the present invention has a low ethoxylate to alkyl ratio and an in another embodiment the surfactant system of the present invention has a low ethoxylate to alkyl ratio and an increased C9-C11/C12-C16 chain length ratio.

Level of Ethoxylation

The ethoxylate to alkyl ratios of the present invention is from about 0.001 to about 0.45 ethoxylate, in one embodiment the ethoxylate to alkyl ratio is from about 0.025 to about 0.40, in another embodiment the ethoxylate to alkyl ratio is from about 0.05 to about 0.35, in yet another embodiment the ethoxylate to alkyl ratio is from about 0.075 to about 0.30, and in yet another embodiment the ethyoxylate to alkyl ratio is from about 0.10 to about 0.25.

The ethoxylate to alkyl ratio is calculated by the following: For each surfactant, the average molecular weight is calculated based on the measured average chain length and average moles of ethoxylation, which can be determined by suitable analytical techniques including Mass Spectrometry. The average ethoxylate weight % is calculated for each surfactant by dividing the molecular weight of the ethoxylated portion of the molecule (based on above average moles of ethoxylation) by the total average molecular weight. Similarly, the average alkyl weight % is calculated for each surfactant by dividing the molecular weight of the alkyl portion of the molecule (based on above average chain lengths) by the total average molecular weight. See Example 1 for example calculations of the average chain length and the average moles of ethoxylation for each surfactant. See Example 1 for example calculations of the average molecular weight, the weight % ethoxylate and the weight % alkyl for each surfactant. The compositional % ethoxylate and % alkyl are computed by multiplying these computed weight % ethoxylate and weight % alkyl values for each surfactant by each surfactant's overall weight percentage in the composition and then summing the values for every surfactant present within the composition. The compositional Ethoxylate/Alkyl ratio is then computed by dividing the overall compositional % ethoxylate value by the overall compositional % alkyl value.

Carbon (Alkyl) Chain Length

Additionally, a synergy has been identified between level of ethoxylation and carbon chain length. It has been found that increasing the C9-C11/C12-C16 chain length ratio results in a further increase in lather performance when used with the abovementioned reduced ethoxylate/alkyl ratio. In one embodiment the C9-C11/C12-C16 chain length ratio is from about 0.10 to about 0.975, in another embodiment the C9-C11/C12-C16 chain length ratio is from about 0.20 to about 0.95, in another embodiment C9-C11/C12-C16 chain length ratio is from about 0.30 to about 0.925, and in yet another embodiment the C9-C11/C12-C16 chain length ratio is from about 0.40 to about 0.90.

The ethoxylate/alkyl ratio is calculated by the following: The C9 to C11 alkyl weight % is calculated for each surfactant by summing the normalized percentages of chain lengths between C9 and C11 and multiplying this proportion by the cumulative calculated average alkyl weight %. Similarly, the C12 to C16 alkyl weight % is calculated for each surfactant by summing the above normalized percentages of chain lengths between C12 and C16 and multiplying this proportion by the cumulative calculated average alkyl weight %. The chain length distributions can be seen in Table 4 and the calculations of C9 to C11 weight % and C12 to C16 weight % are demonstrated in Table 5. The compositional C9 to C11 alkyl % and C12 to C16 alkyl % are computed by multiplying these computed C9 to C11 alkyl weight % and C12 to C16 alkyl weight % values for each surfactant by each surfactant's overall weight percentage in the composition and then summing the values for every surfactant present within the composition. The compositional C9-C11/C12-C16 ratio is then computed by dividing the overall compositional C9 to C11 alkyl % by the overall compositional C12 to C16% as are displayed in Tables 2 and 3.

Surfactants

The Dissolvable Articles of the present invention can comprise one or more surfactants suitable for use on the hair or skin. Suitable surfactants include, but are not limited to, anionic surfactants, nonionic surfactants, cationic surfactants, zwitterionic surfactants, amphoteric surfactants, and combinations thereof. In addition to providing the cleansing and lathering components, the surfactant may also provide the stable porous structure of the present invention.

Anionic surfactants suitable for use in the compositions include alkyl and alkyl ether sulfates. These materials have the respective formulae ROSO3M and RO(C2H4O)xSO3M, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Preferably, R has from about 8 to about 18 carbon atoms, more preferably from about 10 to about 16 carbon atoms, even more preferably from about 11 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Synthetic alcohols may include the grades available via Shell Chemical Co. under the NEODOL trade name as NEODOL 91 (C9-11 alcohols), NEODOL 23 (C12-13 alcohols), NEODOL 25 (C12-15 alcohols), NEODOL 45 (C14-15 alcohols), and NEODOL 135 (C11-C13-C15 alcohols). Lauryl alcohol and straight chain alcohols derived from coconut oil or palm kernel oil are preferred. Such alcohols are reacted with between about 0 and about 10, in one embodiment from about 2 to about 5, in another embodiment about 3, molar proportions of ethylene oxide, and the resulting mixture of molecular species having, for example, an average of 3 moles of ethylene oxide per mole of alcohol, is sulfated and neutralized.

Other suitable anionic surfactants are the water-soluble salts of organic, sulfuric acid reaction products conforming to the formula [R1-SO3-M] where R1 is a straight or branched chain, saturated, aliphatic hydrocarbon radical having from about 8 to about 24, preferably about 10 to about 18, carbon atoms; and M is a cation described hereinbefore.

Still other suitable anionic surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic surfactants suitable for use in the compositions are the succinnates, examples of which include disodium N-octadecylsulfosuccinnate; disodium laurylsulfosuccinate; diammonium laurylsulfosuccinate; tetrasodium N-(1,2-dicarboxyethyl)-N-octadecylsulfosuccinnate; diamyl ester of sodium sulfosuccinic acid; dihexyl esters of sodium sulfosuccinic acid; and dioctyl esters of sodium sulfosuccinic acid.

Other suitable anionic surfactants include olefin sulfonates having about 10 to about 24 carbon atoms. In addition to the true alkene sulfonates and a proportion of hydroxy-alkane-sulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the compositions are the beta-alkyloxy alkane sulfonates. These surfactants conform to the formula

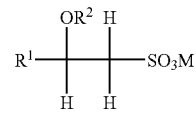

where R1 is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Additional anionic surfactants suitable for use in the compositions include ammonium lauryl sulfate, ammonium laureth sulfate, ammonium laureth-1 sulfate, ammonium laureth-2 sulfate, ammonium laureth-3 sulfate, triethanolamine lauryl sulfate, triethanolamine laureth sulfate, triethanolamine laureth-1 sulfate, triethanolamine laureth-2 sulfate, triethanolamine laureth-3 sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, monoethanolamine lauryl sulfate, sodium tridecyl benzene sulfonate, sodium dodecyl benzene sulfonate, sodium cocoyl isethionate, ammonium decyl sulfate, sodium decyl sulfate, ammonium undecyl sulfate, and ammonium undecyl sulfate and combinations thereof.

In one embodiment of the present invention, one or more of the surfactants is an alkyl sulfate. In one embodiment the one or more alkyl sulfates has an average moles of ethoxylation of from about 0.0 to about 1.9, in another embodiment the one or more alkyl sulfates has an average moles of ethoxylation of from about 0.0 to about 1.5, and in yet another embodiment the one or more alkyl sulfates has an average moles of ethoxylation of from about 0.0 to about 1.0. In one embodiment the one or more alkyl sulfates comprises an ammonium counter ion. Suitable examples of such surfactants with an ammonium counter ion include, but are not limited to, ammonium lauryl sulfate, ammonium laureth-1 sulfate, ammonium laureth-2 sulfate, and combinations thereof.

In one embodiment, one or more anionic surfactants are selected from alkyl sulfates with the following structure:

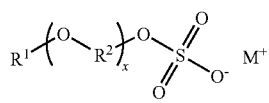

wherein R¹ is selected from C-linked monovalent substituents selected from the group consisting of substituted or unsubstituted, straight or branched alkyl or unsaturated alkyl systems comprising an average of 9.0 to 11.9 carbon atoms; R² is selected from the group consisting of C-linked divalent straight or branched alkyl systems comprising 2 to 3 carbon atoms; M⁺ is a monovalent counterion selected from sodium, ammonium or protonated triethanolamine; and x is 0.0 to 3.0. In one embodiment, one or more of the alkyl sulfate surfactants according to the above structure comprise an average moles of ethoxylation of from about 0.0 to about 1.9, in another embodiment the alkyl sulfate surfactants according to the above structure comprise an average moles of ethoxylation of from about 0.0 to about 1.5, and in yet another embodiment the alkyl sulfate surfactants according to the above structure comprise an average moles of ethoxylation of from about 0.0 to about 1.0. Suitable examples include ammonium decyl sulfate, sodium decyl sulfate, ammonium undecyl sulfate, sodium undecyl sulfate, triethanolamine decyl sulfate, or triethanolamine undecyl sulfate. In one embodiment the anionic surfactant of the present invention includes ammonium undecyl sulfate.

The surfactants of the present invention may also include one or more amphoteric surfactants, zwitterionic surfactants, and/or combinations thereof. Suitable amphoteric or zwitterionic surfactants for use in the composition herein include those which are known for use in hair care or other personal care cleansing. Non limiting examples of suitable zwitterionic or amphoteric surfactants are described in U.S. Pat. Nos. 5,104,646 (Bolich Jr. et al.), 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable examples of such amphoteric surfactants include, but are not limited to, sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and combinations thereof.

In one embodiment, the amphoteric surfactant is a surfactant according to the following structure:

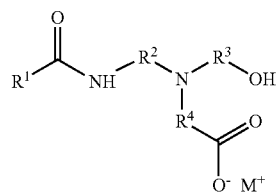

wherein R1 is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; R2, R3, and R4 are each independently selected from the group consisting of C-linked divalent straight alkyl systems comprising 1 to 3 carbon atoms, and C-linked divalent branched alkyl systems comprising 1 to 3 carbon atoms; and M+ is a monovalent counterion selected from the group consisting of sodium, ammonium and protonated triethanolamine. Specific examples of suitable surfactants include sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, and triethanolamine cocoamphoacetate and mixtures thereof.

Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Suitable zwitterionic surfactants include, but are not limited to, cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and combinations thereof.

The compositions of the present invention may further comprise additional surfactants for use in combination with the detersive surfactant component described herein. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

Water-Soluble Polymer ("Polymer Structurant")

The present invention comprises water-soluble polymer that functions as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have a solubility in water, measured at 25° C., of from about 0.1 gram/liter (g/L) to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The terms "water-soluble polymer" and "polymer structurant" are used interchangeably herein. Furthermore, whenever the singular term "polymer" is stated, it should be understood that the term is broad enough to include one polymer or a mixture of more than one polymer. For instance, if a mixture of polymers is used, the polymer solubility as referred to herein would refer to the solubility of the mixture of polymers, rather than to the solubility of each polymer individually.

The one or more water-soluble polymers of the present invention are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous solid.

The water-soluble polymer(s) of the present invention can include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymer(s) of the present invention may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers are also useful as water-soluble polymer(s) in the present invention. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

Suitable water-soluble polymers of the present invention include polyvinyl alcohols, polyvinylpyrrolidones, polyalkylene oxides, starch and starch derivatives, pullulan, gelatin, hydroxypropylmethylcelluloses, methycelluloses, and carboxymethycelluloses.

More preferred water-soluble polymers of the present invention include polyvinyl alcohols, and hydroxypropylmethylcelluloses. Suitable polyvinyl alcohols include those available from Celanese Corporation (Dallas, Tex.) under the Celvol trade name including, but not limited to, Celvol 523, Celvol 530, Celvol 540, Celvol 518, Celvol, 513, Celvol 508, Celvol 504, and combinations thereof. Suitable hydroxypropylmethylcelluloses include those available from the Dow Chemical Company (Midland, Mich.) under the Methocel trade name including, but not limited, to Methocel E50, Methocel E15, Methocel E6, Methocel E5, Methocel E3, Methocel F50, Methocel K100, Methocel K3, Methocel A400, and combinations thereof including combinations with above mentioned hydroxypropylmethylcelluloses.

In a particular embodiment, the above mentioned water-soluble polymer(s) of the present invention may be blended with any single starch or combination of starches as a filler material in such an amount as to reduce the overall level of water-soluble polymers required, so long as it helps provide the dissolvable porous solid with the requisite structure and physical/chemical characteristics as described herein. In such instances, the combined weight percentage of the water-soluble polymer(s) and starch-based material generally ranges from about 10% to about 40 wt %, in one embodiment from about 12 to about 30%, and in a particular embodiment from about 15% to about 25% by weight relative to the total weight of the porous solid. The weight ratio of the water-soluble polymer(s) to the starch-based material can generally range from about 1:10 to about 10:1, in one embodiment from about 1:8 to about 8:1, in still another embodiment from about 1:7 to about 7:1, and in yet another embodiment from about 6:1 to about 1:6.

Typical sources for starch-based materials of the present invention can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof.

The starch-based materials of the present invention may also include native starches that are modified using any modification known in the art, including physically modified starches examples of which include sheared starches or thermally-inhibited starches; chemically modified starches including those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof; conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

Plasticizer

The porous dissolvable solids of the present invention comprise a water soluble plasticizing agent suitable for use in personal care compositions. Non-limiting examples of suitable plasticizing agents include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Examples of polycarboxylic acids include, but are not limited to citric acid, maleic acid, succinic acid, polyacrylic acid, and polymaleic acid. Examples of suitable polyesters include, but are not limited to, glycerol triacetate, acetylated-monoglyceride, diethyl phthalate, triethyl citrate, tributyl citrate, acetyl triethyl citrate, acetyl tributyl citrate. Examples of suitable dimethicone copolyols include, but are not limited to, PEG-12 dimethicone, PEG/PPG-18/18 dimethicone, and PPG-12 dimethicone. Other suitable platicizers of the present invention include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of C2-C10 alcohols and acids); and any other water soluble plasticizer known to one skilled in the art of the foods and plastics industries; and mixtures thereof. Preferred placticizers include glycerin and propylene glycol. European Patent Number EP283165B1 discloses other suitable plasticizers, including glycerol derivatives such as propoxylated glycerol.

Optional Ingredients

The Article may further comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials.

Product Form

The Dissolvable Article of the present invention can be produced in any of a variety of product forms, including dissolvable porous solids used alone or in combination with other personal care components. The dissolvable porous solids can be continuous or discontinuous when used in the personal care compositions. Regardless of the product form, the key to all of the product form embodiments contemplated within the scope of the method of the present invention is the selected and defined dissolvable porous solid that comprises a combination of a solid polymeric structurant and a surfactant-containing active ingredient, all as defined herein.

The Dissolvable Article of the present invention are preferably in the form of one or more flat sheets or pads of an adequate size to be able to be handled easily by the user. It may have a square, rectangle or disc shape or any other shape. The pads can also be in the form of a continuous strip including delivered on a tape-like roll dispenser with individual portions dispensed via perforations and or a cutting mechanism. Alternatively, the dissolvable porous solids of the present invention are in the form of one or more cylindrical objects, spherical objects, tubular objects or any other shaped object. The dissolvable porous solids of the present invention can have a thickness (caliper) of from about 0.5 mm to about 10 mm, in one embodiment from about 1 mm to about 7 mm, and in still another embodiment from about 2 mm to about 6 mm. In the case of cylindrical, spherical, or other objects with more of a third dimension versus a pad or strip, the thickness is taken as the maximum distance of the shortest dimension, i.e., the diameter of a sphere or cylinder for instance.

The Dissolvable Article of the present invention may comprise one or more textured, dimpled or otherwise topographically patterned surfaces including letters, logos or figures. The textured substrate preferably results from the shape of the substrate, in that the outermost surface of the substrate contains portions that are raised with respect to other areas of the surface. The raised portions can result from the formed shape of the article, for example the article can be formed originally in a dimpled or waffle pattern. The raised portions can also be the result of creping processes, imprinted coatings, embossing patterns, laminating to other layers having raised portions, or the result of the physical form of the dissolvable porous solid substrate itself. The texturing can also be the result of laminating the substrate to a second substrate that is textured.

In a particular embodiment, the Dissolvable Article of the present invention can be perforated with holes or channels penetrating into or through the porous solid. These perforations can be formed during the drying process via spikes extended from the surface of the underlying mold, belt or other non-stick surface. Alternatively, these perforations can be formed after the drying process via poking or sticking the porous solids with pins, needles or other sharp objects. Preferably, these perforations are great in number per surface area, but not so great in number so as to sacrifice the integrity or physical appearance of the porous solid. It has been found that such perforations increase the dissolution rate of the porous solids into water relative to un-perforated porous solids.

The Dissolvable Article of the present invention can also be delivered via a water insoluble implement or device. For instance, they may be attached or glued by some mechanism to an applicator to facilitate application to hair and/or skin, i.e., a comb, wrag, wand, or any other conceivable water-insoluble applicator. Additionally, the dissolvable porous solids may be adsorbed to the surfaces a separate high surface area water-insoluble implement, i.e., a porous sponge, a puff, a flat sheet etc. For the latter, the Dissolvable Article of the present invention may be adsorbed as a thin film or layer.

Product Types

Non-limiting examples of product type embodiments for use by the Dissolvable Article and methods of the present invention include hair conditioning substrates, moisturizing substrates, other hair treatment substrates, other skin or body treatment substrates, shaving preparation substrates, pet care substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and the like.

Method of Manufacture

The dissolvable articles of the present invention can be prepared by the process comprising: (1) Preparing a processing mixture comprising surfactant(s), dissolved polymer structurant, plasticizer and other optional ingredients; (2) Aerating the mixture by introducing a gas into the mixture; (3) Forming the aerated wet mixture into a desired one or more shapes; and (4) Drying the aerated wet mixture to a desired final moisture content (e.g., from about 0.1 to 25% moisture, by addition of energy).

Preparation of Processing Mixture

The processing mixture is generally prepared by dissolving the polymer structurant in the presence of water, plasticizer and other optional ingredients by heating followed by cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the surfactant(s), the plasticizer, and other optional ingredients including stepwise processing via pre-mix portions of any combination of ingredients.

The processing mixtures of the present invention comprise: from about 20% to about 50% solids, in one embodiment from about 25% to about 45% solids, and in another embodiment from about 30% to about 40% solids, by weight of the processing mixture before drying; and have a viscosity of from about 5,000 cps to about 150,000 cps, in one embodiment from about 7,500 cps to about 125,000 cps, in another embodiment from about 10,000 cps to about 100,000 cps, and in still another embodiment from about 12,500 cps to about 75,000 cps. The processing mixture viscosity values can be measured on a suitable rheometer, such as a TA Instruments AR500Rheometer with 4.0 cm diameter parallel plate and 1,200 micron gap at a shear rate of 1.0 reciprocal seconds for a period of 30 seconds at 25° C. (available from TA Instruments, New Castle, Del.), or on a standard viscometer, such as a Brookfield Model DV-1 PRIME Digital Viscometer with CP-41 and CP-42 spindles at a shear rate of 1.0 reciprocal seconds for a period of 2 minutes at 25° C. (available from Brookfield Engineering Laboratories, Inc., Middleboro, Mass.). The % solids content is the summation of the weight percentages by weight of the total processing mixture of all of the solid, semi-solid and liquid components excluding water and any obviously volatile materials such as low boiling alcohols.

Aeration of Processing Mixture

The aeration of the processing mixture is accomplished by introducing a gas into the mixture, preferably by mechanical mixing energy but also may be achieved via chemical means. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), or (iii) spray-drying the processing mixture in order to form aerated beads or particles that can be compressed such as in a mould with heat in order to form the porous solid.

In a particular embodiment, it has been discovered that the dissolvable porous solids of the present invention can be prepared within semi-continuous and continuous pressurized aerators that are conventionally utilized within the foods industry in the production of marshmallows. Suitable pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), and the Preswhip (Hosokawa Micron Group, Osaka, Japan).

Forming the Aerated Wet Processing Mixture

The forming of the aerated wet processing mixture may be accomplished by any suitable means to form the mixture in a desired shape or shapes including, but not limited to (i) depositing the aerated mixture to specially designed moulds comprising a non-interacting and non-stick surface including Teflon, metal, HDPE, polycarbonate, neoprene, rubber, LDPE, glass and the like; (ii) depositing the aerated mixture into cavities imprinted in dry granular starch contained in a shallow tray (Starch moulding forming technique widely utilized in the confectionery industry); and (iii) depositing the aerated mixture onto a continuous belt or screen comprising any non-interacting or non-stick material Teflon, metal, HDPE, polycarbonate, neoprene, rubber, LDPE, glass and the like which may be later stamped, cut, embossed or stored on a roll.

Drying the Formed Aerated Wet Processing Mixture

The drying of the formed aerated wet processing mixture may be accomplished by any suitable means including, but not limited to: (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, (x) conveyor driers, (xi) microwave drying technology, and combinations thereof. Preferably, any suitable drying means that does not comprise freeze-drying can be used.

Optional ingredients may be imparted during any of the above described four processing steps or even after the drying process.

The dissolvable porous solids of the present invention may also be prepared with chemical foaming agents by in-situ gas formation (via chemical reaction of one or more ingredients, including formation of $CO_2$ by an effervescent system).

Methods of Use

The Dissolvable Article of the present invention may be used for treating mammalian keratinous tissue such as hair and/or skin, and provide rapid rinse-ability. The method for conditioning the hair may comprise the steps of: a) applying an effective amount of the dissolvable porous solid to the hand, b) wetting the dissolvable porous solid with water and rubbing to dissolve the solid, c) applying the dissolved material to either the hair or skin such as to treat, and d) rinsing the diluted treatment from the hair or skin using water. These steps can be repeated as many times as desired to achieve the desired treatment benefit.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams per dose, preferably from about 0.7 grams to about 5 grams per dose, and more preferably from about 0.9 grams to about 3 grams per dose.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Example 1

Calculation of Surfactant % Ethoxylate and % Alkyl Chain Lengths

This example demonstrates the calculation of the weight percentage of % ethoxylate, % alkyl, % C9-C11, % C12-16 alkyl, the C9-C11/C12-C16 Ratio and the EO/Alkyl Ratio for the surfactants demonstrated in the examples. The normalized distribution of alkyl chain lengths and degree of ethoxylation is determined by Mass Spectrometry as displayed in the below tables:

| | C8 | C9 | C10 | C11 | C12 | C13 | C14 | C15 | C16 | C18 | Average Chain Length |
|---|---|---|---|---|---|---|---|---|---|---|---|
| Ammonium Undecyl Sulfate | 0 | 0 | 0.6 | 93.6 | 5.1 | 0.7 | 0 | 0 | 0 | 0 | 11.1 |
| Ammonium Lauryl Sulfate | 0 | 0.3 | 1.1 | 0.5 | 70.6 | 1.1 | 20.9 | 1.6 | 4.1 | 0.0 | 12.6 |
| Ammonium Laureth-1 Sulfate | 0 | 0.3 | 1.3 | 0.5 | 69.6 | 1.1 | 21.8 | 1.2 | 4.2 | 0 | 12.6 |
| Ammonium Laureth-3 Sulfate | 0 | 0.3 | 0.9 | 0.5 | 71.5 | 1 | 20 | 1.9 | 3.9 | 0 | 12.6 |
| Cocamide Monoethanolamine | 5 | 0 | 6 | 0 | 50 | 0 | 19 | 0 | 10 | 10 | 13.1 |
| Cetyl Alcohol | 0 | 0 | 0 | 0 | 0 | 0 | 0.2 | 0 | 95.1 | 4.7 | 16.1 |

| | E0 | E1 | E2 | E3 | E4 | E5 | E6 | E7 | E8 | E9 | E10 | Average Moles of Ethoxylation |
|---|---|---|---|---|---|---|---|---|---|---|---|---|
| Ammonium Undecyl Sulfate | 0 | 0 | 0 | 0 | 0 | 0 | 0 | 0 | 0 | 0 | 0 | 0 |
| Ammonium Lauryl Sulfate | 0 | 0 | 0 | 0 | 0 | 0 | 0 | 0 | 0 | 0 | 0 | 0 |
| Ammonium Laureth-1 Sulfate | 58 | 21 | 11 | 5.5 | 2.4 | 1 | 0.5 | 0.3 | 0.1 | 0.1 | 0.1 | 0.82 |
| Ammonium Laureth-3 Sulfate | 31 | 17 | 16 | 14 | 9.7 | 5.7 | 3.1 | 1.9 | 1.3 | 0 | 0 | 2.02 |

For each surfactant, the average molecular weight is calculated based on the above measured average chain length and average moles of ethoxylation. The average ethoxylate weight % is calculated for each surfactant by dividing the molecular weight of the ethoxylated portion of the molecule (based on above average moles of ethoxylation) by the total average molecular weight. Similarly, the average alkyl weight % is calculated for each surfactant by dividing the molecular weight of the alkyl portion of the molecule (based on above average chain lengths) by the total average molecular weight. The C9 to C11 alkyl weight % is calculated for each surfactant by summing the above normalized percentages of chain lengths between C9 and C11 and multiplying this proportion by the cumulative calculated average alkyl weight %. Similarly, the C12 to C16 alkyl weight % is calculated for each surfactant by summing the above normalized percentages of chain lengths between C12 and C16 and multiplying this proportion by the cumulative calculated average alkyl weight %. These calculations for the surfactants demonstrated in the examples are given below:

Example 2

(Comparative) Retail Liquid Hair Shampoo Product (Pantene Pro-V)

A liquid hair shampoo product is purchased for comparison purposes to the present invention. The liquid shampoo product is Pantene Pro-V 2 in 1 Smooth & Sleek shampoo+conditioner, 750 ml, which is distributed by Procter and Gamble, Cincinnati, Ohio. The product could be purchased in 2008 and has a lot number 3101LCH. The ingredients include: Water, Ammonium Laureth Sulfate, Ammonium Lauryl Sulfate, Glycol Distearate, Dimethicone, Cetyl Alcohol, Sodium Chloride, Cocamide MEA, Fragrance, Polyquaternium-10, Sodium Citrate, Hydrogenated Polydecene, Sodium Benzoate, Disodium EDTA, PEG-7M, Trimethylolpropane Tricaprylate/Tricaprate, Citric Acid, Panthenol, Panthenyl Ethyl Ether, Ammonium Xylenesulfonate, Methylchloroisothiazolinone, and Methylisothiazolinone. The retail liquid hair shampoo product has an overall surfactant concentration of approximately 18.4 percent by weight of the liquid composition wherein the surfactant concentrations

|  | Calculated Average Molecular Weight | Calculated Ethoxylate Weight % | Calculated Average Alkyl Weight % | Calculated C9 to C11 Alkyl Weight % | Calculated C12 to C16 Alkyl Weight % |
|---|---|---|---|---|---|
| Ammonium Undecyl Sulfate | 270.2 | 0.0% | 57.8% | 54.4% | 3.4% |
| Ammonium Lauryl Sulfate | 291.9 | 0.0% | 60.9% | 1.2% | 59.7% |
| Ammonium Laureth-1 Sulfate | 328.1 | 11.0% | 54.2% | 1.1% | 53.1% |
| Ammonium Laureth-3 Sulfate | 380.7 | 23.4% | 46.7% | 0.8% | 45.9% |
| Cocamide Monoethanolamine | 260.3 | 0.0% | 70.8% | 4.2% | 55.9% |
| Cetyl Alcohol | 243.7 | 0.0% | 93.0% | 0.0% | 88.6% |

For the compositional calculations of ethoxylate weight %, alkyl weight %, C9 to C11 alkyl weight % and C12 to C16 alky weight %, the weight percentage of each surfactant in the composition is multiplied by the above calculated figures and then summed to give an overall respective value for each composition. The compositional C9-C11/C12-C16 ratio is calculated by dividing the C9-C11 wt % by the C12-C16 wt %. Similarly, the compositional Ethoxylate/Alkyl ratio is calculated by dividing the ethoxylate weight % by the alkyl weight %.

are approximately 10% Ammonium Laureth-3 Sulfate, 6% Ammonium Lauryl Sulfate, 1.5% Cocamide MEA, and 0.9% Cetyl Alcohol.

Examples 3-8

Surfactant/Polymer Liquid Processing Compositions

The following surfactant/polymer liquid processing compositions are prepared at the indicated weight percentages as described below. The liquid formulations differ in the type of anionic surfactants

| Component | Ex. 3 AP | Ex. 4 PA | Ex. 5 AP-1 | Ex. 6 PA-1 |
|---|---|---|---|---|
| Glycerin[1] | 3 | 3.0 | 3 | 3.0 |
| Polyvinyl alcohol[2] | 7.3 | 7.3 | 7.3 | 7.3 |
| Ammonium Laureth-3 sulfate (25% activity)[3] | 40.4 | 24.2 | 40.0 | 24.0 |
| Ammonium Undecyl sulfate (24% activity)[4] | 0.0 | 0.0 | 9.9 | 9.9 |
| Ammonium Laureth-1 sulfate (70% activity)[5] | 0.0 | 0.0 | 0.0 | 0.0 |
| Ammonium Lauryl sulfate (25% activity)[6] | 24.2 | 40.4 | 24.0 | 40.0 |
| Cocamide MEA[7] | 1.5 | 1.5 | 0.0 | 0.0 |
| Cetyl Alcohol[8] | 0.9 | 0.9 | 0.0 | 0.0 |
| Distilled water | 22.7 | 22.7 | 15.8 | 15.8 |
| Total | 100.0 | 100.0 | 100.0 | 100.0 |
| Viscosity (cp) | 8,100 | 14,400 | 9,400 | 9,500 |
| % Surfactant | 18.6% | 18.6% | 18.4% | 18.4% |
| Wet Ethoxylate Level (wt. %) | 4.7% | 2.8% | 4.7% | 2.8% |
| Wet C9 to C11 Chain Length Level (wt. %) | 0.2% | 0.2% | 1.4% | 1.5% |
| Wet C12 to C16 Chain Length Level (wt. %) | 9.9% | 10.5% | 8.3% | 8.8% |
| Ratio of C9-C11/C12-C16 | 0.02 | 0.02 | 0.17 | 0.17 |
| Ratio of Ethoxylate/Alkyl | 0.46 | 0.26 | 0.48 | 0.27 |

-continued

| Component | Ex. 7 PA-2 | Ex. 8 ALT |
|---|---|---|
| Glycerin[1] | 3.0 | 3.0 |
| Polyvinyl alcohol[2] | 7.3 | 7.3 |
| Ammonium Laureth-3 sulfate (25% activity)[3] | 6.0 | 7.5 |
| Ammonium Undecyl sulfate (24% activity)[4] | 9.9 | 34.9 |
| Ammonium Laureth-1 sulfate (70% activity)[5] | 6.4 | 12.1 |
| Ammonium Lauryl sulfate (25% activity)[6] | 40.0 | 0.0 |
| Cocamide MEA[7] | 0.0 | 0.0 |
| Cetyl Alcohol[8] | 0.0 | 0.0 |
| Distilled water | 27.5 | 35.3 |
| Total | 100.0 | 100.0 |
| Viscosity (cp) | 10,700 | 5,300 |
| % Surfactant | 18.4% | 18.7% |
| Wet Ethoxylate Level (wt. %) | 1.2% | 1.8% |
| Wet C9 to C11 Chain Length Level (wt. %) | 1.5% | 4.7% |
| Wet C12 to C16 Chain Length Level (wt. %) | 9.1% | 5.6% |
| Ratio of C9-C11/C12-C16 | 0.16 | 0.83 |
| Ratio of Ethoxylate/Alkyl | 0.11 | 0.18 |

[1]Superol K, USP FCC EP Glycerin, supplier: Procter & Gamble Chemicals
[2]Sigma-Aldrich Catalog No. 363081, MW 85,000-124,000, 87-89% hydrolyzed
[3]Ammonium Laureth-3 Sulfate at 25% active with an estimated C8/C9/C10/C11/C12/C13/C14/C15/C16/C18 alkyl chain length distribution of 0/0.3/0.9/0.5/71.5/1/20/1.9/3.9/0 and an average of 2.0 moles of ethoxylation, supplier: Procter & Gamble Chemicals
[4]Ammonium Undecyl Sulfate at 24% active with an estimated C8/C9/C10/C11/C12/C13/C14/C15/C16/C18 alkyl chain length distribution of 0/0/0.6/93.6/5.1/0.7/0/0/0/0, supplier: Procter & Gamble Chemicals
[5]Ammonium Laureth-1 Sulfate at 70% active with an estimated C8/C9/C10/C11/C12/C13/C14/C15/C16/C18 alkyl chain length distribution of 0/0.3/1.3/0.5/69.6/1.1/21.8/1.2/4.2/0 and an average of 0.82 moles of ethoxylation, supplier: Procter & Gamble Chemicals
[6]Ammonium Lauryl Sulfate at 25% active with an estimated C8/C9/C10/C11/C12/C13/C14/C15/C16/C18 alkyl chain length distribution of 0/0.3/1.1/0.5/70.6/1.1/20.9/1.6/4.1/0, supplier: Procter & Gamble Chemicals
[7]NINOL COMF, supplier: Stepan Company, Northfield, IL.
[8]CO-1694 CETYL ALCOHOL NF, supplier: Procter & Gamble Chemicals A target weight of 300 grams, for each of the above compositions, is prepared with the use of a conventional overhead stirrer (IKA® RW20DZM Stirrer available from IKA® Works, Inc., Wilmington, Del.) and a hot plate (Corning Incorporated Life Sciences, Lowell, Mass.). Into an appropriately sized and cleaned vessel, the distilled water and glycerin are added with stirring at 100-150 rpm until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 75 to 80 C after which surfactants are added. The mixture is then heated to 85 C while continuing to stir and then allowed to cool to room temperature. Additional distilled water is added to compensate for water lost to evaporation (based on the original tare weight of the container). The final pH is between 5.2-6.6 and adjusted with citric acid or diluted sodium hydroxide if necessary. The viscosity of the mixture is measured and recorded.

Examples 10-15

Dissolving Porous Shampoo Solids Comprising Different Surfactant Systems and Densities The dissolving porous shampoo solid Examples 10, 11, 12, 13, 14 and 15 are prepared from the surfactant/polymer liquid processing solutions from Examples 3, 4, 5, 6, 7, and 8 respectively, as described below and summarized in the below table.

|  | Ex. 10.1 | Ex. 10.2 | Ex. 11.1 | Ex. 11.2 |
|---|---|---|---|---|
| Surfactant weight % (pre-drying) | 18.6 | 18.6 | 18.6 | 18.6 |
| Ethoxylate weight % (pre-drying) | 3.2% | 3.2% | 1.9% | 1.9% |
| C11 chain length weight % (pre-drying) | 0.0% | 0.0% | 0.0% | 0.0% |
| Aeration Time (sec) | 130 | 70 | 255 | 130 |
| Wet Density (g/cm^3) | 0.17 | 0.21 | 0.19 | 0.22 |
| Drying temperature (degrees Celsius) | 75 | 75 | 75 | 75 |
| Average dry pad weight (g) | 0.56 | 0.74 | 0.64 | 0.70 |
| Average dry pad thickness (cm) | 0.56 | 0.52 | 0.59 | 0.54 |
| Average dry pad density (g/cm^3) | 0.06 | 0.08 | 0.06 | 0.08 |
| Average dry pad basis weight (g/m^2) | 332 | 437 | 378 | 415 |
| Dry pad surfactant weight %[1] | 61.3% | 61.3% | 61.3% | 61.3% |
| Ethoxylate/Alkyl Ratio | 0.46 | 0.46 | 0.26 | 0.26 |
| C9 to C11 Chain Length Level (wt. %)[1] | 0.7% | 0.7% | 0.8% | 0.8% |
| C12 to C16 Chain Length Level (wt. %)[1] | 32.7% | 32.7% | 34.5% | 34.5% |
| Ratio of C9-C11/C12-C16[1] | 0.02 | 0.02 | 0.02 | 0.02 |

-continued

|  | Ex. 12.1 | Ex. 12.2 | Ex. 13.1 | Ex. 13.2 |
|---|---|---|---|---|
| Surfactant weight % (pre-drying) | 18.4 | 18.4 | 18.4 | 18.4 |
| Ethoxylate weight % (pre-drying) | 3.2% | 3.2% | 1.9% | 1.9% |
| C11 chain length weight % (pre-drying) | 1.4% | 1.4% | 1.4% | 1.4% |
| Aeration Time (sec) | 90 | 60 | 117 | 82 |
| Wet Density (g/cm$^3$) | 0.18 | 0.21 | 0.18 | 0.22 |
| Drying temperature (degrees Celsius) | 75 | 75 | 75 | 75 |
| Average dry pad weight (g) | 0.54 | 0.65 | 0.58 | 0.73 |
| Average dry pad thickness (cm) | 0.46 | 0.49 | 0.55 | 0.50 |
| Average dry pad density (g/cm$^3$) | 0.07 | 0.08 | 0.06 | 0.09 |
| Average dry pad basis weight (g/m$^2$) | 322 | 386 | 344 | 431 |
| Dry pad surfactant weight %[1] | 61.0% | 61.0% | 61.0% | 61.0% |
| Ethoxylate/Alkyl Ratio | 0.48 | 0.48 | 0.27 | 0.27 |
| C9 to C11 Chain Length Level (wt. %)[1] | 4.8% | 4.8% | 4.8% | 4.8% |
| C12 to C16 Chain Length Level (wt. %)[1] | 27.4% | 27.4% | 29.2% | 29.2% |
| Ratio of C9-C11/C12-C16[1] | 0.17 | 0.17 | 0.17 | 0.17 |

|  | Ex. 14.1 | Ex. 14.2 | Ex. 15.1 | Ex. 15.2 |
|---|---|---|---|---|
| Surfactant weight % (pre-drying) | 18.4 | 18.4 | 18.7 | 18.7 |
| Ethoxylate weight % (pre-drying) | 1.1% | 1.1% | 1.7% | 1.7% |
| C11 chain length weight % (pre-drying) | 1.4% | 1.4% | 4.8% | 4.8% |
| Aeration Time (sec) | 130 | 105 | 100 | 80 |
| Wet Density (g/cm$^3$) | 0.18 | 0.23 | 0.18 | 0.21 |
| Drying temperature (degrees Celsius) | 75 | 75 | 75 | 75 |
| Average dry pad weight (g) | 0.63 | 0.75 | 0.59 | 0.70 |
| Average dry pad thickness (cm) | 0.49 | 0.47 | 0.44 | 0.47 |
| Average dry pad density (g/cm$^3$) | 0.08 | 0.09 | 0.08 | 0.09 |
| Average dry pad basis weight (g/m$^2$) | 374 | 444 | 347 | 413 |
| Dry pad surfactant weight %[1] | 61.0% | 61.0% | 61.4% | 61.4% |
| Ethoxylate/Alkyl Ratio | 0.11 | 0.11 | 0.18 | 0.18 |
| C9 to C11 Chain Length Level (wt. %)[1] | 4.9% | 4.9% | 15.3% | 15.3% |
| C12 to C16 Chain Length Level (wt. %)[1] | 30.3% | 30.3% | 18.5% | 18.5% |
| Ratio of C9-C11/C12-C16[1] | 0.16 | 0.16 | 0.83 | 0.83 |

[1]Calculated assuming a residual 5 weight percent moisture content.

250 grams of the surfactant/polymer liquid processing solution (from Examples 1 through 7) is transferred into a 5 quart stainless steel bowl of a KitchenAid® Mixer Model K5SS (available from Hobart Corporation, Troy, Ohio) and fitted with a flat beater attachment. The mixture is vigorously aerated at a maximum speed setting of 10 until a wet density of approximately 0.18 grams per cubic centimeter or 0.22 grams per cubic centimeter is achieved (times recorded in table). The density is measured by weighing a filling a cup with a known volume and evenly scraping off the top of the cup with a spatula. The resulting aerated mixture is then spread with a spatula into square 160 mm×160 mm aluminum molds with a depth of 6.5 mm with the excess wet foam being removed with the straight edge of a large metal spatula that is held at a 45 degrees angle and slowly dragged uniformly across the mold surface. The aluminum molds are then placed into a 75 C convection oven for approximately 120 minutes or until the weight loss due to evaporation is between 67% and 69% of the original foam weight within each mold. The molds are allowed to cool to room temperature with the substantially dry porous solids removed from the molds with the aid of a thin spatula and tweezers.

Each of the resulting 160 mm×160 mm square pads is cut into nine 43 mm×43 mm squares (with rounded edges) using a cutting die and a Samco SB20 cutting machine (each square representing surface area of approximately 16.9 square centimeters). The resulting smaller pads are then stored within zip-lock bags. The individual average pad weight and individual average pad thickness is measured.

Note that any actives and/or compositions disclosed herein can be used in and/or with the articles, and in particular the household care articles, disclosed in the following U.S. patent applications, including any publications claiming priority thereto: U.S. 61/229,981; U.S. 61/229,986; U.S. 61/229,990; U.S. 61/229,996; U.S. 61/230,000; and U.S. 61/230,004. Such articles may comprise one or more of the following: detersive surfactant; plasticizer; enzyme; suds suppressor; suds booster; bleach; bleach stabilizer; chelant; cleaning solvent; hydrotrope; divalent ion; fabric softener additive (e.g. quaternary ammonium compounds); nonionic surfactant; perfume; and/or a perfume delivery system. Such articles may be utilized in methods including, but not limited to: dosing into a washing machine to clean and/or treat fabric; dosing into a dishwasher to clean and/or treat cutlery; and dosing into water to clean and/or treat fabric and/or hard surfaces.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable article in the form of a porous dissolvable solid structure, comprising:
   (a) from about 23% to about 75% surfactant, wherein said surfactant has an average ethoxylate/alkyl ratio of from about 0.001 to about 0.45, and wherein said surfactant comprises a C9-C11/C12-C16 alkyl chain length ratio of from about 0.05 to about 0.99;
   (b) from about 10% to about 50% water soluble polymer; and
   (c) from about 1% to about 15% plasticizer;
      wherein said dissolvable article has a density of from about 0.03 g/cm³ to about 0.20 g/cm³, and wherein the dissolvable article has a percent open cell content of from about 80 to about 100%; wherein all percentages are weight percentages based on the total weight of said dissolvable article, and wherein all ratios are weight ratios.

2. The dissolvable article of claim 1, wherein said Ethoxylate/Alkyl ratio is from about 0.025 to about 0.40.

3. The dissolvable article of claim 2, wherein said Ethoxylate/Alkyl ratio is from about 0.05 to about 0.35.

4. The dissolvable article of claim 2, wherein said Ethoxylate/Alkyl ratio is from about 0.075 to about 0.30.

5. The dissolvable article of claim 2, wherein said Ethoxylate/Alkyl ratio is from about 0.10 to about 0.25.

6. The dissolvable article of claim 1, wherein said C9-C11/C12-C16 alkyl chain length ratio is from about 0.10 to about 0.975.

7. The dissolvable article of claim 1, wherein said C9-C11/C12-C16 alkyl chain length ratio is from about 0.20 to about 0.95.

8. The dissolvable article of claim 1, wherein said C9-C11/C12-C16 alkyl chain length ratio is from about 0.30 to about 0.925.

9. The dissolvable article of claim 1, wherein said C9-C11/C12-C16 alkyl chain length ratio is from about 0.40 to about 0.90.

10. The dissolvable article of claim 1, wherein one or more surfactants are anionic surfactants.

11. The dissolvable article of claim 10, wherein said anionic surfactants are alkyl sulfates.

12. The dissolvable article of claim 11, wherein said alkyl sulfate surfactants comprise an average moles of ethoxylation of from about 0.0 to about 1.9.

13. The dissolvable article of claim 12, wherein said alkyl sulfate surfactants comprise an average moles of ethoxylation of from about 0.0 to about 1.5.

14. The dissolvable article of claim 13, wherein said alkyl sulfate surfactants comprise an average moles of ethoxylation of from about 0.0 to about 1.0.

15. The dissolvable article according to claim 11, wherein said alkyl sulfate comprises an ammonium counter ion.

16. The dissolvable article according to claim 10, wherein said one or more anionic surfactants is selected from the group consisting of ammonium lauryl sulfate, ammonium laureth-1 sulfate, ammonium laureth-2 sulfate, and combinations thereof.

17. The dissolvable article of claim 10, wherein said anionic surfactant is an alkyl sulfate according to the following structure:

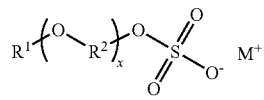

wherein R¹ is a C-linked monovalent substituent selected from the group consisting of substituted alkyl systems comprising an average of from about 9 to about 11.9 carbon atoms, unsubstituted alkyl systems comprising about 9 to about 11 carbon atoms, straight alkyl systems comprising an average of from about 9 to about 11.9 carbon atoms, branched alkyl systems comprising an average of from about 9.0 to about 11.9 carbon atoms, and unsaturated alkyl systems comprising an average of from about 9 to about 11.9 carbon atoms; R² is selected from the group consisting of C-linked divalent straight alkyl systems comprising 2 to 3 carbon atoms, and C-linked divalent branched alkyl systems comprising 2 to 3 carbon atoms; M⁺ is a monovalent counterion selected from a group consisting of sodium, ammonium and triethylammonium; and x is 0 to 3.

18. The dissolvable article according to claim 17, wherein said R¹ C-linked monovalent substituents comprises an average value of from about 10.0 to about 11.75 carbon atoms.

19. The dissolvable article according to claim 17, wherein said R1 C-linked monovalent substituents comprises an average value of from about 10.75 to about 11.25 carbon atoms.

20. The dissolvable article according to claim 10, wherein one or more of the anionic surfactants are selected from ammonium decyl sulfate, sodium decyl sulfate, ammonium undecyl sulfate, sodium undecyl sulfate and combinations thereof.

21. The dissolvable article according to claim 10, wherein one or more of the anionic surfactants are selected from ammonium decyl sulfate, ammonium undecyl sulfate and combinations thereof.

22. The dissolvable article according to claim 1, wherein said porous dissolvable solid has a cellular interconnectivity defined by having a Star Volume of from about 1 mm³ to about 90 mm³; and a Structure Model Index that is non-negative and ranges from about 0.0 to about 3.0.

23. The dissolvable article of claim 1, wherein said water soluble polymer has a weighted average molecular weight of from about 40,000 to about 500,000.

24. The dissolvable article of claim 1, wherein said article is a non-freeze-dried article.

25. A dissolvable article in the form of a porous dissolvable solid structure, wherein said article is formed by a process comprising the steps of:
   a. preparing a pre-mix, wherein said pre-mix comprises a surfactant, a water soluble polymer, a plasticizer, one or more surfactants wherein said surfactant has an average ethoxylate/alkyl ratio of from about 0.001 to about 0.45, wherein said surfactant comprises a C9-C11/C12-C16 alkyl chain length ratio of from about 0.05 to about 0.99, wherein said pre-mix has from about 20% to about 50% solids and a viscosity of from about 5000 cps to about 150,000 cps, wherein all percentages are weight percentages based on the total weight of said pre-mix, and wherein all ratios are weight ratios;
   b. aerating said pre-mix by introducing a gas into said pre-mix to form a wet aerated pre-mix;
   c. forming the wet aerated pre-mix into a desired one or more shapes to form a shaped wet pre-mix; and d. forming said dissolvable article by drying said shaped wet pre-mix into a final moisture content, wherein said final moisture content is from about 0.1% to about 25% moisture, wherein said dissolvable article has a density of from about 0.03 g/cm³ to about 0.20 g/cm³, and wherein the dissolvable article has a percent open cell content of from about 80 to about 100% and wherein all percentages are weight percentages based on the total weight of said dissolvable article.

* * * * *